United States Patent [19]

Fenstermacher et al.

[11] 4,190,662
[45] Feb. 26, 1980

[54] HALOMETHYL SUBSTITUTED DIALKOXYPYRIDINES

[75] Inventors: Myk R. Fenstermacher, Baton Rouge, La.; Robert L. Noveroske, Midland, Mich.

[73] Assignee: The Dow Chemical Company, Midland, Mich.

[21] Appl. No.: 889,179

[22] Filed: Mar. 23, 1978

[51] Int. Cl.² ............. A01N 9/22; C07D 213/61; C07D 213/64
[52] U.S. Cl. ................. 424/263; 546/303; 546/345
[58] Field of Search ............. 260/297 R; 424/263; 546/303

[56] References Cited

U.S. PATENT DOCUMENTS

| | | | |
|---|---|---|---|
| 3,244,722 | 4/1966 | Johnston et al. | 260/297 X |
| 3,609,158 | 9/1971 | Torba | 260/297 R X |
| 3,711,486 | 1/1973 | Torba | 424/263 X |
| 3,787,420 | 1/1974 | Torba | 260/294.9 |
| 4,062,962 | 12/1977 | Noveroske | 424/263 |
| 4,143,144 | 3/1979 | Tobol et al. | 424/263 |

OTHER PUBLICATIONS

Klingsberg, Pyridine and Derivatives, Part Two, pp. 346-347, Interscience Publishers, Inc., NY (1961).

*Primary Examiner*—John D. Randolph
*Attorney, Agent, or Firm*—S. Preston Jones; C. Kenneth Bjork; Ronald G. Brookens

[57] ABSTRACT

Compounds are prepared which correspond to the formula

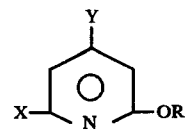

wherein X and Y represent OR', trichloromethyl, trifluoromethyl, dichloromethyl, dichlorofluoromethyl or chlorodifluoromethyl with the proviso that one of X or Y must be OR' and the other of X and Y is other than OR'; and R and R' each independently represent alkyl of 1 to 12 carbons or alkenyl of 3 or 4 carbon atoms. These compounds and compositions containing them have been found to be useful as agronomic fungicides, especially useful and valuable for the control of soil-borne plant disease organisms which attack the roots of plants.

38 Claims, No Drawings

HALOMETHYL SUBSTITUTED DIALKOXYPYRIDINES

DESCRIPTION OF THE PRIOR ART

In U.S. Pat. No. 3,244,722, issued April 5, 1966, there are described and claimed, among other related compounds, those corresponding to the formula

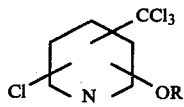

wherein R is alkyl of 1 to 18 carbon atoms or lower alkenyl.

Exemplary compounds listed in this patent include 2-chloro-4-methoxy-6-(trichloromethyl)pyridine, 2-chloro-6-methoxy-4-(trichloromethyl)pyridine, 5-chloro-2-methoxy-4-(trichloromethyl)pyridine, and 3-chloro-2-methoxy-4-(trichloromethyl)pyridine. As reported in this patent, various compounds disclosed therein are useful as herbicides; various other compounds are useful in the control of pest fish and aquatic insects; and other compounds are taught to be useful as insecticides and anthelmintic agents for warm-blooded animals.

In U.S. Pat. No. 4,062,962, issued Dec. 13, 1977, a select group of the compounds taught in U.S. Pat. No. 3,244,722 are taught as fungicides for the control of soil-borne plant disease organisms which attack the roots of plants.

In U.S. Pat. No. 3,983,238, issued Sept. 28, 1976, there are described and claimed compounds having anticoccidal activity and of the formula:

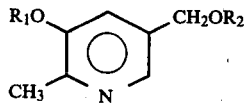

wherein $R_1$ and $R_2$ are each hydrogen, aliphatic acyl, aromatic acyl or heterocyclic acyl with at least $R_1$ or $R_2$ being heterocyclic acyl.

Other related known prior art includes U.S. Pat. No. 3,317,542, issued May 2, 1967 which is directed to compounds of the formula

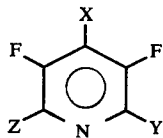

wherein X, Y and Z may be the same or different and each represents a list of groups including alkoxy and methyl. The utility of these compounds is not set forth.

SUMMARY OF THE INVENTION

The present invention is directed to compounds corresponding to the formula

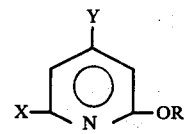

In this and succeeding formulae, X and Y each represent OR', trichloromethyl, trifluoromethyl, dichloromethyl, dichlorofluoromethyl or chlorodifluoromethyl with the proviso that one of X or Y must be OR' and the other of X and Y is other than OR'; and R and R' each independently represent alkyl of 1 to 12 carbon atoms or alkenyl of 3 or 4 carbon atoms.

In the present specification and claims, the term "alkyl" designates a straight or branched chain saturated aliphatic hydrocarbon group containing from 1 to 12 carbon atoms, inclusive, such as, for example, methyl, ethyl, propyl, isopropyl, butyl, secondary-butyl, tertiary-butyl, amyl, isoamyl, hexyl, secondary-hexyl, heptyl, octyl, nonyl, decyl, dodecyl, 4-methyldecyl, undecyl, 3-ethylnonyl, 2-ethylhexyl and 3-propylheptyl. The term "alkenyl" as employed in the present specification and claims designates straight or branched chain alkenyl groups of 3 or 4 carbon atoms, inclusive, such as, for example, 2-propenyl, 2-butenyl, 3-butenyl, 2-isobutenyl and 2-secondary butenyl.

The pyridine compounds of the present invention are crystalline solids or oils and are of low solubility in water and of moderate solubility in common organic solvents.

The pyridine compounds of the present invention and compositions containing said compounds have been found useful, as agronomic fungicides, especially useful and valuable for the control of soil-borne plant root disease organisms.

The compounds of the present invention can be prepared by the reaction of an appropriate halomethyl substituted halopyridine reactant with an appropriate alkali metal alkoxide or alkenoxide in the presence of a reaction medium. This reaction can be represented as follows:

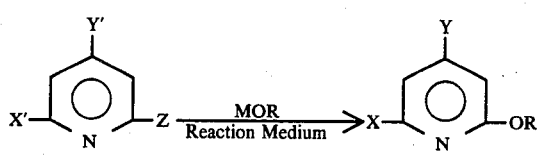

In the above reaction representation, no attempt has been made to present a balanced equation. In addition, Y' and X' represent chloro, bromo, fluoro, trichloromethyl, trifluoromethyl, dichloromethyl, dichlorofluoromethyl or chlorodifluoromethyl with the proviso that one Y' or X' must be chloro, bromo or fluoro and the other of Y' and X' must be other than chloro, bromo or fluoro; Y, X and R are as hereinbefore defined; Z represents chloro, fluoro, bromo or OR and M represents sodium, potassium, lithium, or cesium.

In carrying out the above reaction, the appropriate halomethyl substituted halopyridine reactant is mixed with the appropriate alkali metal alkoxide or alkenoxide and the reaction medium and the mixture heated at a temperature of from about 50° C. up to the reflux temperature of the mixture until the reaction is complete. The reaction is usually complete in from about 1 to about 168 hours, depending upon the specific reactants and solvents employed.

After the completion of the reaction, the reaction mixture is usually diluted with water and extracted with a solvent such as methylene chloride, petroleum ether, hexane or toluene. The extract is thereafter usually washed with water, dried, filtered and the solvent removed by evaporation or other conventional separatory procedures. The product is thereafter recovered and, if desired, can be purified by various conventional techniques such as crystallization and/or recrystallization from solvents such as, for example, methanol, methylene chloride, hexane, or toluene or by distillation depending upon whether the product is a solid or oil.

Since many 2- or 4-halomethyl-2 or 4-halo-6-alkoxy or alkenoxy pyridines are known as taught in U.S. Pat. No. 3,244,722, it is within the scope of the present invention to employ such compounds as starting materials. In such procedures, this reactant is mixed with the desired MOR reactant as hereinabove set forth, and the reaction proceeds as outlined hereinbefore. By following this procedure, compounds can be prepared wherein both of the OR substituents are the same; wherein one R substituent is alkyl and the other R substituent is alkenyl or wherein one R substituent is alkyl or alkenyl of a given chain length and the other R substituent is alkyl or alkenyl of another chain length.

In addition to the above, it is also within the scope of the present invention to employ a 2,4-di halo-6-(halomethyl)pyridine or 2,6-di halo-4-(halomethyl)pyridine as starting material and to react these materials with the desired MOR reactant as set forth herein above. In addition, by carefully controlling the reaction, compounds can be prepared wherein both of the R substituents are the same; or by carrying out the reaction in sequential steps employing the appropriate MOR reactants for each step thus obtaining products wherein one R substituent is alkyl and the other R substituent is alkenyl or wherein one R substituent is alkyl or alkenyl of a given chain length and the other R substituent is alkyl or alkenyl of another chain length.

In carrying out the above preparations, the amounts of the reactants employed are not critical as some of the desired product is formed with any amounts. However, since the reaction consumes the reactants, equimolar proportions (1 molar equivalent of the alkali metal alkoxide or alkenoxide per halogen atom to be reacted) for the most part should be employed. It has, however, been found, that when preparing compounds wherein both halogens are reacted or wherein the last halogen is being reacted, that an increase in the yield of the desired product can be obtained by employing an excess of the alkali metal alkoxide or alkenoxide. Therefore, it is preferred to employ from about 1.5 to about 6 molar equivalents or more of the alkali metal alkoxide or alkenoxide per halogen atom to be reacted.

Representative reaction media useful for carrying out the above preparations include, for example, dimethylsulfoxide, alkanols and alkenols of the same carbon content as the alkoxide or alkenoxide employed for the reaction, dimethoxyethane or diglyme.

When carrying out the methods of preparation as outlined hereinabove, it is within the scope of this invention to convert the halomethyl group of an existing product to a different halomethyl group thereby forming a different halomethyl compound. For example, a compound of the present invention containing a trichloromethyl group can be dehalogenated, with a dehalogenation agent such as, for example, stannous chloride or zinc metal, in the presence of concentrated hydrochloric acid and a solvent, to the dichloromethyl analog under conventional conditions.

In such a procedure, a solution of the trichloromethyl substituted pyridine compound in a solvent such as acetone, or other conventional solvent for this reaction, is contacted and refluxed with a solution containing an excess of the dehalogenation agent dissolved in one of the above solvents. The reaction is usually straight forward and is complete in from about 1 to about 4 hours.

DESCRIPTION OF SOME PREFERRED EMBODIMENTS

In order that the present invention can be more fully understood, the following examples are given primarily by way of illustration and should not be construed as limitations upon the overall scope of the same.

EXAMPLE I—2,6-Dimethoxy-4-(trichloromethyl)pyridine

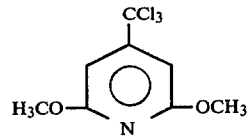

A solution was prepared by refluxing 2.64 gram-moles of 2,6-dichloro-4-(trichloromethyl)pyridine in 2 liters of methanol. To this solution was added over about a 2 hour period a solution of 3 gram-moles of sodium methalate in 1.5 liters of methanol. The mixture was refluxed for ~6 hours. The mixture was cooled and filtered to remove insoluble by-products. The methanol was thereafter removed and the solid 2,6-dimethoxy-4-(trichloromethyl)pyridine product was recovered by filtration. The product melted at 70°–73° C. and was found to have carbon, hydrogen and nitrogen contents of 37.70, 2.80 and 5.40 percent, respectively, as compared to the theoretical contents of 37.46, 3.12 and 5.46 percent, respectively, as calculated for the above-named compound. The structure was also confirmed by nuclear magnetic resonance spectroscopy (NMR).

EXAMPLE II—2,6-Dimethoxy-4-(trichloromethyl)pyridine

In another procedure, 2,6-dimethoxy-4-(trichloromethyl)pyridine was prepared by dissolving 4.6 grams (0.2 mole) of sodium metal in 200 milliliters (ml) of methanol. This solution was quickly added to a solution of 26.09 grams (0.1 mole) of 6-chloro-2-methoxy-4-(trichloromethyl)pyridine in 100 ml of dimethylsulfoxide. The mixture was refluxed at ~75° C. for ~12 hours and ~25 ml of methanol was removed resulting in a reflux temperature of 78° C. An additional 50 ml of dimethylsulfoxide was added thereto and refluxing continued for ~5½ hours at 85° C. An additional 50 ml of methanol was removed and additional dimethylsulfoxide was added and refluxing continued at 95° C. for ~5 hours. The mixture was thereafter diluted with water and extracted with methylene chloride. The methylene chloride layer was washed thoroughly with water and dried over sodium sulfate. The oily product which remained was crystallized from methanol to give 11.2 grams (~44 percent of theoretical) of the desired 2,6-dimethoxy-4-(trichloromethyl)pyridine which melted at 71°-73° C. The structure of the compound was confirmed by NMR.

EXAMPLE III—2,6-Diethoxy-4-(trichloromethyl)pyridine

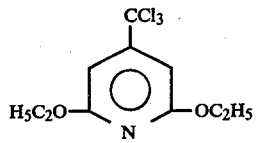

A solution was prepared by dissolving 17.24 grams (0.75 mole) of sodium metal in 400 ml of ethanol. To this solution was rapidly added a solution prepared by dissolving 137.48 grams (0.5 mole) of 6-chloro-2-ethoxy-4-(trichloromethyl)pyridine in 300 ml of ethanol at 35° C. The mixture was heated to reflux at 72° for ~42 hours and thereafter a solution of 8.62 grams of sodium metal dissolved in 200 ml of ethanol was added thereto and the mixture refluxed for about an additional 5 hours. The mixture was diluted with 500 ml of water after first removing 500 ml of ethanol. The mixture was extracted twice with methylene chloride and the methylene chloride layers combined and washed with water (an emulsion formed and ammonium chloride was added thereto and the mixture allowed to set 3 days (week-end) for the emulsion to break). The methylene chloride layer was dried over sodium sulfate, treated with activated charcoal and filtered. The methylene chloride was removed by evaporation and 150 ml of methanol was added thereto. The mixture was chilled and the 2,6-diethoxy-4-(trichloromethyl)pyridine product which precipitated was separated. The product was recrystallized from 150 ml of methanol and dried over methylene chloride. The product melted at 45.5°-47.0° C. and was recovered in a yield of 46 grams (32 percent of theoretical). The product was found by analysis to have carbon, hydrogen, and nitrogen contents of 42.12, 4.17 and 4.92 percent, respectively, as compared with the theoretical contents of 42.20, 4.25 and 4.92 percent, respectively, as calculated for the above-named compound. The structure of the compound was confirmed by NMR.

EXAMPLE IV—2,6-Dimethoxy-4-(dichloromethyl)pyridine

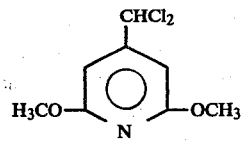

A solution was prepared by dissolving 19.63 grams (0.087 mole) of stannous chloride, dihydrate in 100 ml of acetone. To this mixture was added 7.3 ml of concentrated hydrochloric acid. The mixture was stirred for ~10 minutes. To this mixture was added a solution prepared by dissolving 12.8 grams (0.05 mole) of 2,6-dimethoxy-4-(trichloromethyl)pyridine in 40 ml of acetone at 30° C. The mixture was heated to reflux (60° C.) and refluxed for ~3½ hours. The reaction mixture was cooled to ~15° C. and the acetone was removed at this temperature. The residual material was mixed with ~250 ml of water and raised to a pH of ~12 with ~20-30 ml of a 50 percent sodium hydroxide solution. The mixture was extracted twice with 250 ml portions of warm (60°-100° C.) petroleum ether and the petroleum ether extract washed twice with water. The petroleum ether extract was dried over sodium sulfate, filtered and the ether removed by evaporation. The desired 2,6-dimethoxy-4-(dichloromethyl)pyridine product was recovered from the residue by crystallization from hexane. The product melted at 59°-62° C. and was recovered in a yield of 7.3 grams (65.8 percent of theoretical). Upon analysis, the product was found to have carbon, hydrogen, nitrogen and chlorine contents of 43.44, 4.08, 6.32 and 31.68 percent, respectively, as compared to the theoretical contents of 43.26, 4.08, 6.30 and 31.93 percent, respectively, as calculated for the above-named compound. The structure of the compounds was confirmed by NMR.

EXAMPLE V—2,6-Dimethoxy-4-(difluorochloromethyl)pyridine

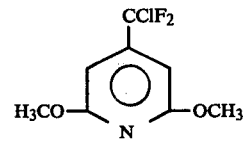

To a solution of 11.62 grams (0.05 mole) of 2,6-dichloro-4-(chlorodifluoromethyl)pyridine dissolved in 32 ml of dimethylsulfoxide was added a solution of 2.64 grams (0.115 mole) of sodium metal dissolved in 65 ml of methanol in five increments as follows: (1) 15 ml of the solution were added and the temperature rose to 38° C. The mixture was stirred 5 minutes and (2) 10 ml of the solution were added and the temperature rose to 42° C., the mixture was stirred for 5 minutes and cooled to 38° C.; (3) 10 ml of the solution were added and the temperature rose to 40° C., the mixture was stirred for 5 minutes and cooled to 35° C.; (4) 20 ml of the solution were added, no exotherm occurred; and (5) 10 ml of the solution were added and the mixture stirred for 5 minutes. The mixture was then heated and refluxed for 7 hours. The reaction mixture was cooled and diluted with 400 ml of water and extracted twice with methylene chloride. The methylene chloride layer was washed with water, dried with sodium sulfate and the methylene chloride removed by evaporation. The 2,6-dimethoxy-4-(difluorochloromethyl)pyridine product was dried over chloroform and was recovered in a yield of 9.5 grams (85 percent of theoretical). The product had a refractive index of n25/d=1.4747 and upon analysis, was found to have carbon, hydrogen, nitrogen and chlorine contents of 42.84, 3.82, 6.28 and 16.02 percent, respectively, as compared with the theoretical contents of 42.97, 3.60, 6.26 and 15.80 percent, as calculated for the above-named structure. The structure of the compounds was confirmed by NMR.

EXAMPLE VI—2,6-Dimethoxy-4-(trifluoromethyl)pyridine

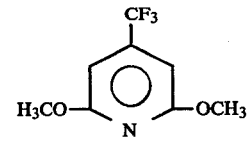

To a solution of 10.80 grams (0.05 mole) of 2,6-dichloro-4-(trifluoromethyl)pyridine dissolved in 32 ml of dimethylsulfoxide was slowly added portionwise, with stirring, a solution of 2.64 grams (0.115 mole) of sodium metal dissolved in 65 ml of methanol. The mixture was heated to reflux (75° C.) and maintained under reflux for 3½ hours. After cooling, the mixture was diluted with 500 ml of water and extracted twice with 250 ml portions of methylene chloride. The solvent extract was washed with water, dried with sodium sulfate and filtered. The methylene chloride was removed by evaporation and the 2,6-dimethoxy-4-(trifluoromethyl)pyridine product crystallized from methanol. The product was dried over carbon tetrachloride and recovered in a yield of 6 grams (58 percent of theoretical) and melted at 26°-27° C. The structure was confirmed by NMR and upon analysis, the product was found to have carbon, hydrogen and nitrogen contents of 49.47, 5.30 and 6.24 percent, respectively, as compared with the theoretical contents of 46.38, 3.89 and 6.76 percent, respectively, as calculated for the above-named compound.

EXAMPLE
VII—2,4-Dimethoxy-6-(trichloromethyl)pyridine

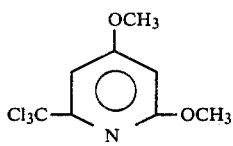

To a solution of 13.27 grams (0.05 mole) of 2,4-dichloro-6-(trichloromethyl)pyridine dissolved in 32 ml of dimethylsulfoxide was slowly added over thirty minutes, with stirring, a solution of 2.64 grams (0.12 mole) of sodium metal dissolved in 65 ml of methanol. The mixture was heated to reflux (75° C.) for 2 hours and allowed to sit overnight at room temperature. The mixture was diluted with 450 ml of water and extracted with methylene chloride. The extract was washed with water, dried with sodium sulfate, filtered and evaporated to dryness. The crude 2,4-dimethoxy-6-trichloromethyl)pyridine product was recovered by crystallization from 25 ml of chilled methanol. The product was further refined by recrystallization from pentane followed by recrystallization from chilled methanol. The product melted at 47.5°-49° C. and the purest material was recovered in a yield of 3.3 grams (25 percent of theoretical). The structure of the product was confirmed by NMR. Upon analysis, the compound was found to have carbon, hydrogen and nitrogen contents of 38.52, 3.49 and 5.28 percent, respectively, as compared with the theoretical contents of 37.45, 3.14 and 5.46 percent, respectively, as calculated for the above-named compound.

EXAMPLE
VIII—2-Methoxy-6-ethoxy-4-(trichloromethyl)-pyridine

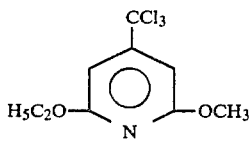

To a solution of 54.99 grams (0.20 mole) of 2-chloro-6-ethoxy-4-(trichloromethyl)pyridine dissolved in 100 ml of methanol at 60° C. was rapidly added a solution of 6.90 grams (0.3 mole) of sodium metal dissolved in 150 ml of methanol. The mixture was heated to reflux for ~1 hour and then stirred at 62° C. overnight and thereafter refluxed for 8 hours followed by stirring at 62° C. overnight and then refluxed for 1 hour. A solution of 3.45 grams of sodium metal dissolved in 75 ml of methanol was added and the mixture brought back to reflux. The mixture was thereafter cooled and covered and allowed to sit ~64 hours (over a weekend). The methanol was removed by evaporation and the residue diluted with water and extracted with methylene chloride. The extract was washed with water, dried with sodium sulfate and the methylene chloride removed by evaporation. The desired 2-methoxy-6-ethoxy-4-(trichloromethyl)pyridine product was recovered by crystallization of the residue from methanol followed by recrystallization from ethanol. The product was recovered in a yield of 8.5 grams and melted at 36°-38° C. Upon analysis, the product was found to have carbon, hydrogen, nitrogen and chlorine contents of 39.49, 3.54, 5.17 and 39.82 percent, respectively, as compared with the theoretical contents of 39.95, 3.72, 5.17 and 39.31 percent, respectively, as calculated for the above-named compound.

EXAMPLE
IX—2-Methoxy-6-butoxy-4-(trichloromethyl)pyridine

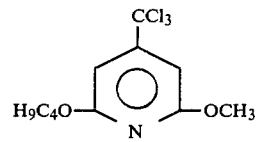

To a solution of 52.19 grams (0.2 mole) of 2-chloro-6-methoxy-4-(trichloromethyl)pyridine dissolved in 100 ml of butanol was added over a 25-minute period a solution of 6.9 grams (0.3 mole) of sodium metal dissolved in 300 ml of butanol. The mixture was heated to 115° C. and held there for ~3 hours. Thereafter, the butanol was removed by evaporation leaving an oily residue. The residue was taken up in methylene chloride, washed with water, (the emulsion formed was dispersed by treatment with ammonium chloride) dried over sodium sulfate and filtered. The methylene chloride was removed leaving an oily material. The desired 2-methoxy-6-butoxy-4-(trichloromethyl)pyridine product was recovered by multiple distillation with the center cut yielding 6.9 grams (11 percent of theoretical) of the product. The product had a refractive index of n25/d=1.5226 and upon analysis, the product was found to have carbon, hydrogen and nitrogen contents of 54.27, 6.25 and 4.51 percent, respectively, as compared with the theoretical contents of 49.35, 5.92 and 4.11 percent, respectively, as calculated for the above-named compound.

By following the general procedures as set forth above and in the examples, the following compounds are prepared.

TABLE I

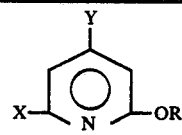

| Y | X | R | Molecular Weight | Refractive Index $n25/d$ |
|---|---|---|---|---|
| —$CCl_3$ | —$OC_3H_7$ | —$C_3H_7$ | 312.63 | |
| —$CCl_3$ | —$OCH_2CH:CH_2$ | —$CH_2CH:CH_2$ | 308.59 | 1.5409 |
| —$CCl_3$ | —$OC_4H_9$ | —$CH_2CH:CHCH_3$ | 324.64 | |
| —$CCl_3$ | —$OC_4H_9$ | —$C_4H_9$ | 340.68 | 1.5131 |
| —$OC_4H_9$ | —$CCl_3$ | —$C_4H_9$ | 340.68 | 1.5110 |
| —$OC_4H_9$ | —$CCl_3$ | —$CH_3$ | 298.60 | |
| —$OCH_3$ | —$CCl_3$ | —$C_4H_9$ | 298.60 | 1.5220 |
| —$CCl_3$ | —$OCH_2(CH_3)CH:CH_2$ | —$CH_2(CH_3)CH:CH_2$ | 338.66 | 1.5309 |
| —$CCl_3$ | —$OCH_2CH:CHCH_3$ | —$CH_2CH:CHCH_3$ | 336.65 | 1.5374 |
| —$CCl_3$ | —$OC_8H_{17}$ | —$C_8H_{17}$ | 452.90 | 1.5082 |
| —$OC_8H_{17}$ | —$CCl_3$ | —$C_8H_{17}$ | 452.90 | |
| —$OCH_3$ | —$CCl_3$ | —$C_8H_{17}$ | 342.70 | |
| —$CCl_3$ | —$OC_8H_{17}$ | —$CH_3$ | 342.70 | 1.5145 |
| —$CCl_3$ | —$OCH_2CH:CH_2$ | —$C_8H_{17}$ | 380.75 | |
| —$CCl_3$ | —$OC_{12}H_{25}$ | —$C_{12}H_{25}$ | 565.11 | |
| —$OC_{12}H_{25}$ | —$CCl_3$ | —$CH_3$ | 410.82 | |
| —$OC_{12}H_{25}$ | —$CCl_3$ | —$C_{12}H_{25}$ | 565.11 | |
| —$CCl_3$ | —$OCH_2(CH_3)CH:CH_2$ | —$C_{12}H_{25}$ | 451.89 | |
| —$CCl_3$ | —$OC_{12}H_{25}$ | —$CH_3$ | 410.82 | 1.5000 |
| —$CCl_3$ | —$OC_{12}H_{25}$ | —$C_8H_{17}$ | 496.99 | |
| —$OC_8H_{17}$ | —$CCl_3$ | —$C_{12}H_{25}$ | 496.99 | |
| —$OC_4H_9$ | —$CCl_3$ | —$C_{12}H_{25}$ | 440.89 | |
| —$OC_2H_5$ | —$CF_3$ | —$C_2H_5$ | 235.22 | |
| —$CF_3$ | —$OC_2H_5$ | —$C_2H_5$ | 235.22 | |
| —$CF_3$ | —$OCH_2CH:CH_2$ | —$CH_2CH:CH_2$ | 259.23 | |
| —$OC_4H_9$ | —$CF_3$ | —$C_4H_9$ | 291.32 | |
| —$CF_3$ | —$OC_4H_9$ | —$C_4H_9$ | 291.32 | |
| —$CF_3$ | —$OCH_2CH:CHCH_3$ | —$CH_2CH:CHCH_3$ | 299.30 | |
| —$OC_4H_9$ | —$CF_3$ | —$CH_3$ | 249.24 | |
| —$CF_3$ | —$OCH_3$ | —$C_4H_9$ | 249.24 | |
| —$CF_3$ | —$OCH_3$ | —$CH_2CH:CH_2$ | 232.19 | |
| —$OC_8H_{17}$ | —$CF_3$ | —$C_8H_{17}$ | 403.53 | |
| —$CF_3$ | —$OCH_2CH:CHCH_3$ | —$C_8H_{17}$ | 345.41 | |
| —$OCH_3$ | —$CF_3$ | —$C_8H_{17}$ | 305.35 | |
| —$OC_8H_{17}$ | —$CF_3$ | —$C_2H_5$ | 319.37 | |
| —$OCH_3$ | —$CF_3$ | —$C_4H_9$ | 249.24 | |
| —$OC_8H_{17}$ | —$CF_3$ | —$C_4H_9$ | 347.39 | |
| —$CF_3$ | —$OC_8H_{17}$ | —$C_4H_9$ | 347.39 | |
| —$CF_3$ | —$OC_{12}H_{25}$ | —$C_{12}H_{25}$ | 515.75 | |
| —$OC_{12}H_{25}$ | —$CF_3$ | —$C_{12}H_{25}$ | 515.75 | |
| —$OCH_3$ | —$CF_3$ | —$C_{12}H_{25}$ | 361.45 | |
| —$CF_3$ | —$OCH_3$ | —$C_{12}H_{25}$ | 361.45 | |
| —$OC_{12}H_{25}$ | —$CF_3$ | —$CH_3$ | 361.45 | |
| —$CF_3$ | —$OC_8H_{17}$ | —$C_{12}H_{25}$ | 459.65 | |
| —$OC_{12}H_{25}$ | —$CF_3$ | —$C_8H_{17}$ | 459.65 | |
| —$CF_3$ | —$OC_4H_9$ | —$C_{12}H_{25}$ | 403.54 | |
| —$CF_3$ | —$OCH_2CH:CH_2$ | —$C_{12}H_{25}$ | 387.49 | |
| —$OCH_3$ | —$CCl_2F$ | —$CH_3$ | 240.06 | |
| —$CCl_2F$ | —$OCH_3$ | —$CH_3$ | 240.06 | 1.5091 |
| —$CCl_2F$ | —$OC_2H_5$ | —$C_2H_5$ | 268.12 | |
| —$CCl_2F$ | —$OCH_2CH:CH_2$ | —$CH_2CH:CH_2$ | 292.14 | |
| —$OC_4H_9$ | —$CCl_2F$ | —$C_4H_9$ | 324.31 | |
| —$OCH_3$ | —$CCl_2F$ | —$C_4H_9$ | 282.14 | |
| —$CCl_2F$ | —$OCH_3$ | —$C_4H_9$ | 282.14 | |
| —$CCl_2F$ | —$OC_8H_{17}$ | —$C_8H_{17}$ | 436.44 | |
| —$CCl_2F$ | —$OCH_3$ | —$C_8H_{17}$ | 338.25 | |
| —$OC_8H_{17}$ | —$CCl_2F$ | —$C_4H_9$ | 380.33 | |
| —$CCl_2F$ | —$OC_8H_{17}$ | —$C_2H_5$ | 352.28 | |
| —$CCl_2F$ | —$OCH_3$ | —$C_{12}H_{25}$ | 394.36 | |
| —$CCl_2F$ | —$OC_{12}H_{25}$ | —$C_{12}H_{25}$ | 548.65 | |
| —$OC_8H_{17}$ | —$CCl_2F$ | —$C_{12}H_{25}$ | 492.55 | |
| —$OC_{12}H_{25}$ | —$CCl_2F$ | —$C_4H_9$ | 436.44 | |
| —$CCl_2F$ | —$OC_2H_5$ | —$C_2H_5$ | 268.12 | |
| —$CCl_2F$ | —$OC_4H_9$ | —$C_4H_9$ | 324.23 | |
| —$CCl_2F$ | —$OC_8H_{17}$ | —$C_8H_{17}$ | 436.44 | |
| —$CCl_2F$ | —$OC_{12}H_{25}$ | —$C_{12}H_{25}$ | 548.66 | |
| —$CCl_2F$ | —$OCH_3$ | —$C_4H_9$ | 282.14 | |
| —$OC_8H_{17}$ | —$CCl_2F$ | —$CH_3$ | 338.25 | |
| —$OC_2H_5$ | —$CCl_2F$ | —$C_8H_{17}$ | 352.28 | |
| —$OC_4H_9$ | —$CCl_2F$ | —$C_{12}H_{25}$ | 436.44 | |
| —$CCl_2F$ | —$OCH_3$ | —$C_{12}H_{25}$ | 408.39 | |
| —$CCl_2F$ | —$OC_8H_{17}$ | —$C_{12}H_{25}$ | 492.55 | |
| —$OCH_3$ | —$CHCl_2$ | —$CH_3$ | 222.07 | |
| —$CHCl_2$ | —$OC_2H_5$ | —$C_2H_5$ | 250.13 | |

TABLE I-continued

![structure: Y on top, X on left, OR on right, N in ring]

| Y | X | R | Molecular Weight | Refractive Index n25/d |
|---|---|---|---|---|
| —CHCl$_2$ | —OC$_4$H$_9$ | —C$_4$H$_9$ | 306.23 | |
| —CHCl$_2$ | —OCH$_2$CH : CH$_2$ | —CH$_2$CH : CH$_2$ | 274.15 | |
| —OC$_8$H$_{17}$ | —CHCl$_2$ | —C$_8$H$_{17}$ | 418.45 | |
| —CHCl$_2$ | —OCH$_3$ | —CH$_2$CH : CH$_2$ | 248.11 | |
| —CHCl$_2$ | —OCH$_3$ | —C$_4$H$_9$ | 263.15 | |
| —OCH$_3$ | —CHCl$_2$ | —C$_8$H$_{17}$ | 320.26 | |
| —OC$_8$H$_{17}$ | —CHCl$_2$ | —C$_2$H$_5$ | 334.29 | |
| —CHCl$_2$ | —OC$_8$H$_{17}$ | —C$_4$H$_9$ | 362.34 | |
| —CHCl$_2$ | —OC$_8$H$_{17}$ | —CH$_2$CH : CHCH$_3$ | 360.33 | |
| —CHCl$_2$ | —OCH$_3$ | —C$_{12}$H$_{25}$ | 376.37 | |
| —OC$_8$H$_{17}$ | —CHCl$_2$ | —C$_{12}$H$_{25}$ | 474.56 | |
| —CHCl$_2$ | —OC$_{12}$H$_{25}$ | —C$_{12}$H$_{25}$ | 530.67 | |
| —CHCl$_2$ | —OC$_4$H$_9$ | —C$_{12}$H$_{25}$ | 418.45 | |
| —CClF$_2$ | —OC$_4$H$_9$ | —C$_4$H$_9$ | 307.77 | |
| —CClF$_2$ | —OCH$_2$CH : CH$_2$ | —C$_4$H$_9$ | 291.73 | |
| —CClF$_2$ | —OCH$_3$ | —C$_4$H$_9$ | 265.69 | |
| —OC$_8$H$_{17}$ | —CClF$_2$ | —C$_8$H$_{17}$ | 441.99 | |
| —OCH$_3$ | —CClF$_2$ | —C$_8$H$_{17}$ | 321.80 | |
| —CClF$_2$ | —OC$_{12}$H$_{25}$ | —C$_{12}$H$_{25}$ | 532.20 | |
| —OC$_8$H$_{17}$ | —CClF$_2$ | —C$_{12}$H$_{25}$ | 471.10 | |

Preparation of Starting Materials 2,6-Dichloro-4-(dichloromethyl)pyridine

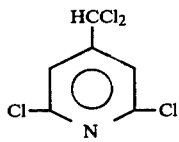

To a solution of 73 grams (0.275 mole) of 2,6-dichloro-4-(trichloromethyl)pyridine dissolved in 125 milliliters of acetone was added a solution of 108 grams (0.48 mole) of stannous chloride hydrate and 40 milliliters of concentrated hydrochloric acid in 500 milliliters of acetone. The mixture was refluxed for 2.0 hours. The solid which formed was separated by filtration and three fourths of the solvent was thereafter removed by evaporation. The remainder of the reaction mixture was diluted with water and the oil phase which formed, removed by extraction with hexane. The 2,6-dichloro-4-(dichloromethyl)pyridine product was dried and recovered from the solvent by evaporation of the solvent. The product had a boiling point of 123°–126° C. at 1.6 millimeters of mercury.

2,6-Dichloro-4-(dichlorofluoromethyl)pyridine

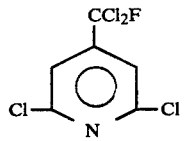

A mixture containing 138.5 grams (0.522 mole) of 2,6-dichloro-4-(trichloromethyl)pyridine and 34 grams (0.187 mole) of antimony trifluoride was heated to 80°–84° C. and maintained under agitation for 23 minutes. During this step, a slow stream of chlorine gas was passed over the surface of the reaction mixture. The reaction mixture was steam distilled and the crude 2,6-dichloro-4-(dichlorofluoromethyl)pyridine was purified by fractionation. The product had a boiling point of 74°–76° C. at 1.0 millimeter of mercury.

The 2,4-dichloro-6-(dichloromethyl)pyridine and the 2,4-dichloro-6-(dichlorofluoromethyl)pyridine reactants can be prepared by following the above procedure, employing 2,4-dichloro-6-(trichloromethyl)pyridine as the starting material.

The 2,4- and 2,6-dibromo or difluoro counterparts of the above dichloro compounds can be prepared by conventional halogen exchange. They can also be prepared by employing the 2,4- or 2,5-dibromo(or difluoro)-6-(or 4)(trichloromethyl)pyridine as the starting material in the above procedure.

The compounds employed as starting materials in the present invention which correspond to one of the formulae

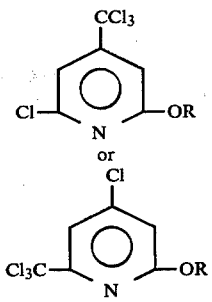

wherein R is as hereinbefore defined, are all known in the art and can be purchased commercially or they can be prepared as taught in U.S. Pat. No. 3,244,722. The compounds can be prepared by reacting 2,6-dichloro-4-(trichloromethyl)pyridine with an alkali metal salt of the appropriate hydroxy(alcohol) compound in a solvent at a temperature of from about 60° to about 120° C. for about 0.5 to 10 hours.

The compounds employed as starting materials of the present invention which correspond to one of the formulae

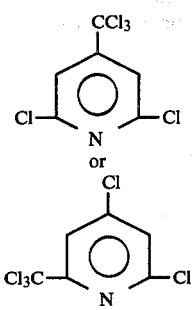

can be prepared as taught in U.S. Pat. No. 3,244,722. This patent teaches that the compounds may be prepared by contacting an appropriate methylpyridine and hydrogen chloride at temperatures of about 50° C. to produce a liquid methylpyridine hydrochloride composition, thereafter passing chlorine gas through the liquid mixture at temperatures of from about 95° to about 110° C. while irradiating the reaction mixture and thereafter fractionally distilling the liquid mixture. The compounds may also be prepared by rapidly mixing in the vapor phase chlorine, an appropriate methylpyridine and an inert diluent such as a perchlorinated hydrocarbon during a brief contact time at temperatures of from about 400° C. to about 490° C. and thereafter cooling to precipitate the desired starting material or fractionally distilling to recover the desired starting material.

The compounds employed as starting materials which correspond to one of the formulae

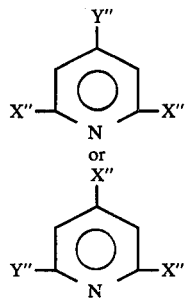

wherein $X'''$ is chloro, bromo or fluoro and $Y'''$ is trifluoromethyl, dichlorofluoromethyl or difluoromethyl can be prepared employing the procedures taught by McBee et al., 2nd Eng. Chem. 39, pages 389–391 (1947) (see Chem. Abstracts, Vol. 41, page 3461d). In this procedure an appropriate 2,4- or 2,6-halogenated 4- or 6-(trichloromethyl)pyridine is treated with HF in an autoclave at temperatures up to 300° C.

It should be further noted that while there are many procedures for preparing the starting materials, they all can be prepared employing the procedures outlined in U.S. Pat. No. 3,244,722 or modifications thereof or combinations of any of the procedures outlined hereinabove.

The compounds of the present invention and formulation containing them have been found to be useful as plant fungicides especially valuable for the control of soil-borne plant root disease organisms which attack the roots of plants. In accordance with the present invention, a method for protecting plants, which are in soil containing soil-borne plant root disease organisms, from attack by said organisms is provided which comprises contacting plants or plant parts with a non-phytotoxic plant protecting amount of at least one of the compounds set forth hereinabove or with a composition (formulation) containing at least one of the compounds.

The mode of action of the active toxicants of the present invention is not fully understood and the present invention should not be considered limited by the specific mode of action. It has, however, been found that, while the active toxicants can, in fact, at high dosage rates actively kill the disease organisms set forth herein above, the use of such rates may be phytotoxic to the plants being treated. It has also been found that the active toxicants of the present invention are effective in eliminating plant root diseases from plants which are infected at the time of treatment and non-infected plants can be protected from attack. As indicated above, the mode of action by which this elimination/protection action of the active compounds occurs is not fully understood. It appears that the pathogencity of the disease organism is suppressed or inhibited or the organism is in some way reduced to a level insufficient for disease expression which allows for normal plant growth.

The present method also offers a practical advantage in that there is no need to employ the additional time and labor required by conventional pre-plant sterilization with soil fumigants.

A further practical advantage of the present method is that the active compounds or toxicants are used in amounts which are the equivalent of ounces of the active ingredient on a per acre basis as against the conventional soil fumigation practices which require pounds and hundreds of pounds of active material per acre.

In the present specification and claims, the term "plant part" is employed to designate all parts of a plant and includes seeds, the underground portion, i.e., bulbs, stolons, tubers, rhizomes, ratoons, corms, the root system, hereinafter commonly referred to as root, and the above-ground portion, i.e., the crown, stalk, stem, foliage or leaf system, fruit or flower.

In the present specification and claims, the term "systemic" defines the translocation of the active compound employed in the present method through the plant whereby they selectively accumulate principally in the underground portions of the plant. The following illustrative example will further the understanding of the term "systemic" as used herein. If the active compounds are applied to seeds, accumulation of the active compound is found mainly in the underground system of the germinating seed; if applied to storage organs (bulbs, stolons, tubers, rhizomes, ratoons or corms), the active compound will absorb into the plant tissue and upon active growth following dormancy, the compound will be found mainly in the below-ground portion of the growing plant; if applied to the above-ground portions of the plant, the active compounds downwardly translocate and principally accumulate in the underground system; and application of the active compound adjacent the underground portions of the plant gives remarkably fast protection by the compound, due to the proximity of the point of application to the area of chemical accumulation, and to the fact there is mainly no translocation away from the underground system.

Compositions containing one or more of the active compounds of the present invention have been found to be very effective in the control of plant root disease in plants either before or after the plant has been attacked by soil-borne plant root disease organisms.

Representative soil-borne plant root disease organisms which attack the below-ground portion of plants, i.e., the root system and which are controlled by the present method include Rhizoctonia, Phytophthora, Pythium, and Aphanomyces.

Control of soil-borne plant disease by the present invention is achieved, for example, in cereal crops such as corn, wheat, barley, rye, oats, rice and sorghum; vegetable crops such as tomatoes, peppers, lettuce, onions, cabbage, broccoli, squash, cucumbers, cauliflower, etc.; legumes such as peanuts, soybeans, beans, peas and alfalfa; root crops such as turnips, beets, carrots, white potatoes, sweet potatoes and yams; fiber crops such as cotton, flax and hemp; fruit crops such as apples, bananas, cantaloupes, cherries, dates, figs, grapes, pineapples, grapefruit, lemons, limes, oranges, peaches, pears, plums, strawberries and watermelon; oil crops such as castorbean, copra, olives, palms, rubber and sunflower; stimulants such as cocoa, coffee, tea and tobacco; sugar crops such as sugar cane and sugar beets; turf including bent grass and blue grass, rye and fescue; ornamentals such as chrysanthemums, zinnias, carnations, lilies, violets, petunias, marigolds, philodendrons, schefflera, dracaena, wax plants, jade plant, ivy, ferns, rubber plants, cactus and dieffenbachia; woody ornamentals such as pines, roses, rhododendrons, azaleas, boxwoods, spruces and the like. While the above lists a variety of crop plants which may be treated by the practice of the present invention, it is to be understood that the present method is not restricted to the above list of crop plants.

Generally in the actual practice of the method of the present invention, a plant protecting amount of the active toxicant compounds can be applied to the plant or plant part by a variety of convenient procedures. Such procedures include soil incorporation whereby compositions containing the active toxicant are mechanically mixed with the soil; applied to the surface of the soil and thereafter dragged, disced or rototilled into the soil; or transported into the soil with a liquid carrier such as by injection, spraying or irrigation. Additionally, a plant protecting amount of the active toxicant compounds can be employed in sprays, gels or coatings for above-ground applications or drenched onto the soil surface. In additional application methods, the active toxicant can be applied by vapor transfer; added in liquid or solid composition to hydroponic operations; seed treatment operations and by conventional plant part coating operations or other techniques known to those skilled in the art. The only limitation upon the mode of application employed is that it must be one which will ultimately allow the toxicant to come in contact with plants or plant parts.

The exact dosage of the active toxicant employed can be varied depending upon the specific plant, its stage of development, hardiness, the mode of application and its growth media. Generally, the active ingredient should be present in an amount equivalent to from about 50 micrograms to about 140 grams or more per plant on a per plant basis. Translating this into conventional application rates, this amount is equivalent to from about 0.0005 pound to about 10 pounds or more of the active ingredient on a per acre, per application basis, as chemical available to the plant.

It will be appreciated that on a per plant basis, seed treatment of small seeded plant species such as grasses, carrots, and the like will actually require much smaller amounts than 50 micrograms per plant. Generally, rates in the range of 1/32 to about 8 ounces per 100 pounds of seeds will be optimum for seed treatment among the diversity of plant species. For practices such as conventional tobacco transplant treatment or in-furrow soil treatment of plants such as soybeans at seeding and the like, an amount of active toxicant approximately equal to 8 to about 32 milligrams would be utilized on a per plant basis.

Larger amounts of the active ingredient may advantageously be applied when treatments are employed which distribute the material throughout the soil. For example, when the active ingredient is applied as an at-plant row treatment or as an early or mid-season post-plant side dress treatment, those amounts of chemical not proximal to plant roots are essentially unavailable to the plant and therefore not effective as set forth hereinabove. In such practices, the amount of the active ingredient employed needs to be increased to rates as high as about 20 pounds per acre or higher to assure that the requisite effective quantity of active ingredient is made available to the plants.

The present invention can be carried out by employing the pyridine compounds directly, either singly or in combination. However, the present invention also embraces the employment of liquids, dusts, wettable powders, granules or encapsulated compositions containing at least one of said compounds as active ingredient. In such usage, the compound or compounds can be modified with one or more of a plurality of additaments or adjuvants including inert solvents, inert liquid carriers and/or surface active dispersing agents and coarsely or finely-divided inert solids. The augmented compositions are also adapted to be employed as concentrates and subsequently diluted with additional inert carrier to produce other compositions in the form of dusts, sprays, granules, washes or drenches. In compositions where the adjuvant is a coarsely or finely-divided solid, a surface active agent or the combination of a surface active agent and a liquid additament, the adjuvant cooperates with the active component so as to facilitate the invention. Whether the composition is employed in liquid, wettable powder, gel, wax, jelly, dust, granule, or encapsulated form, the active compound will normally be present in an amount of from 2 to 98 percent by weight of the total composition.

In the preparation of dust, or wettable powder compositions, the toxicant products can be compounded with any of the finely-divided solids, such as pyrophyllite, talc, chalk, gypsum, fuller's earth, bentonite, attapulgite, modified clays, starch, casein, gluten and the like. In such operations, the finely-divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, organic carriers such as ground corn cobs, walnut hulls, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols, alkyl phenols and the like. Also, oil-soluble ionic emulsifying agents such as mahogany soaps can be used. Suitable inert organic liquid which can be employed in the compositions include petroleum oils and distillates, toluene, liquid halohydrocarbons and synthetic organic oils and vegetable oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° F. Also desirable are those petroleum fractions with higher boiling points which can leave residues due to low vapor pressures, provided they are low in aromatic content such as pariffinic and isopariffinic oils which are of low phytotoxicity potential. The proportion of the compounds of this invention employed in a suitable solvent may vary from about 2 to about 50 percent or higher. Additionally, the active components can be compounded with water or petroleum jellies to prepare the viscous or semi-solid treating compositions.

The expression "soil" is employed herein in its broadest sense to be inclusive of all conventional "soils," as defined in Webster's New International Dictionary, Second Edition, unabridged, published in 1937, G. C. Merriam Co., Springfield, Massachusetts. Thus, the term refers to any substance or medium in which plants may take root and grow, and is intended to include not only earth, but also compost, manure, muck, sand, synthetic growth mediums such as vermiculite and pearlite and the like, adapted to support plant growth. In this context, hydroponic growth mediums are also included.

DESCRIPTION OF SOME PREFERRED EMBODIMENTS FOR USE

In order that the method of the present invention may be more fully understood, the following examples are given to illustrate the manner by which the method can be practiced but, as such, should not be construed as limitations upon the overall scope of the same.

EXAMPLE X

Soil infected with the tobacco black shank pathogen Phytophthora parasitica var. nicotianeae was uniformly mixed and placed in 6-inch pots. To said pots were transplanted six week old tobacco seedlings of the "402" variety which had been grown in pathogen free soil. Test dispersions of 2,6-dimethoxy-4-(trichloromethyl)pyridine were prepared by dissolving 0.48 grams of the chemical in 2-cubic centimeters (cc) acetone containing 20 milligrams (mg) of Tween 85 emulsifier (a proprietary material of Imperial Chemical Industries, U.S., which is a polyoxyethylene (20) sorbitan trioleate) and thereafter diluting the solution with water to prepare dispersions containing 600, 300, and 150 parts by weight of the compound per million parts of the ultimate dispersion. Thereafter, the test dispersions were employed to treat separate pots containing the seedling by pouring 100 cubic centimeters of each of the dispersions onto the soil, assuring root contact with sufficient chemical. Additional pots were treated with an aqueous acetone solution containing no toxicant to serve as controls. After treatments, the plants were maintained under conditions conducive for good plant growth. Three weeks after treatment, the plants were examined for disease control. The results of this examination are set forth below in Table II.

TABLE II

| Active Compound Employed | Application Rate in ppm* | Percent control of Phytophthora parasitica in Tobacco Seedlings 3 weeks |
|---|---|---|
| 2,6-Dimethoxy-4-(trichloromethyl)pyridine | 600 | 100 |
|  | 300 | 100 |
|  | 150 | 66 |
| Acetone Control | — | 0 |

*Equivalent to dosage rate of 1.0, 0.5 and 0.25 pounds of active compound per acre assuming a planting rate of 6,000 plants per acre and a transplant water volume of 200 gallons per acre.

EXAMPLE XI

A concentrate was prepared by admixing 50 mg of 2,6-dimethoxy-4-(trichloromethyl)pyridine with 1 cc of acetone containing 10 mg of Tween 85. Test dispersions were prepared by admixing a predetermined amount of water with a predetermined amount of the concentrate.

Soil infected with soybean root rot disease organism Phytophthora megasperma was uniformly mixed and used to fill 3-inch pots. Five soybean seeds of the variety "Harosoy 63" were planted in each pot with 4 pots being used per treatment. The soil in each pot was drenched with 50 cc of one of the test dilutions. Additional pots were also prepared as above except they were drenched with an acetone-water solution containing no chemical to serve as a control. The pots were thereafter maintained under conditions conducive to good plant growth and to the growth of the root rot organism. Twenty seven days after treatment, the pots were examined to determine the percent of root rot disease control. The results of this study, and the treatment rates are set forth below in Table III.

TABLE III

| Test Compound | Dosage in Parts of Test Compound per Million Parts of the Ultimate Dispersion | Percent Control Of the Root Rot Organism Phytophthora megasperma |
|---|---|---|
| 2,6-Dimethoxy-4-(trichloromethyl)pyridine | 12 | 55 |
|  | 28 | 55 |
|  | 50 | 85 |
|  | 100 | 60 |
| Control | — | 5 |

EXAMPLE XII

Acetone dilutions were prepared by dissolving 2,6-dimethoxy-4-(trichloromethyl)pyridine in predetermined amounts with predetermined amounts of acetone. One milliliter aliquots of each dilution were applied equally to 1-ounce seedlots of soybean seeds of the variety "Harosoy 63". This application procedure resulted in an equivalent to treating 100 pounds of seeds at a dilution rate of 1, 2 and 4 ounces of active compound. Twenty seeds from each treatment were thereafter planted in pots of soil containing the root rot disease organism, *Phytophthora megasperma*. Additional seeds, 20 treated with acetone containing no toxicant and 20 untreated to serve as controls, were planted. After planting, the pots containing the seeds were watered and placed in a greenhouse under conditions conducive to good plant growth and to disease development. Twenty seven days after treatment, the pots were thereafter examined to determine the percent kill and control of the disease organism from each treatment. The results of this examination are set forth below in Table IV.

TABLE IV

| Test Compound | Dosage in Ounces of Active Compound per 100 Pounds of Seeds | Percent Control Of the Root Rot Organism *Phytophthora megasperma* |
|---|---|---|
| 2,6-Dimethoxy-4-(trichloromethyl)pyridine | 1.0 | 60 |
| | 2.0 | 75 |
| | 4.0 | 80 |
| Acetone treated control | — | 7.5 |
| Untreated control | — | 5.0 |

EXAMPLE XIII

A 10 percent granular mixture is prepared by admixing 2.0 grams of 2,6-dimethoxy-4-(trichloromethyl)pyridine with 0.4 grams of the Atlox-846 emulsifier (a proprietary material of Imperial Chemical Industries, U.S., which is a polyoxyethylene sorbitol oleate), 1.6 grams of propylene glycol and 16.0 grams of calcined montmorillionite clay.

Soil infected with the soybean root rot disease organism *Phytophthora megasperma* was uniformly mixed and used to fill 3-inch pots. Five soybean seeds of the variety "Harosoy 63" were planted in each pot, with 4 pots being used per test mixture. The pots were treated by distributing quantities of the above test mixture onto the soil surface and seeds in each pot to give dosages equivalent to 0.25, 0.5, 1.0 and 2.0 pounds of the active material per acre applied as an in-furrow treatment wherein a 1" band of a crop with 36" row spacing is treated. After treatment, sterile potting soil was added to the pots to cover the granular test mixture. Additional pots were also prepared as above and treated with the same granular mixture containing no test compound. The pots were thereafter maintained under conditions conducive to good plant growth and disease development. Twenty seven days after treatment, the pots were examined to determine the percent of disease control. The results of this examination are set forth below in Table V.

TABLE V

| Test Compound | Dosage in Pounds Per Acre In-furrow of Test Compound | Percent Control Of the Root Rot Organism *Phytophthora megasperma* |
|---|---|---|
| 2,6-Dimethoxy-4-(trichloromethyl)pyridine | 1.25 | 85 |
| | 0.50 | 75 |
| | 1.00 | 75 |
| | 2.00 | 80 |

TABLE V-continued

| Test Compound | Dosage in Pounds Per Acre In-furrow of Test Compound | Percent Control Of the Root Rot Organism *Phytophthora megasperma* |
|---|---|---|
| Control | — | 5 |

EXAMPLE XIV

Acetone dilutions were prepared by dissolving predetermined amounts of one of the hereinafter set forth compounds with predetermined amounts of acetone. One milliliter aliquots of each compound at each dilution were applied equally to 1-ounce seedlots of soybean seeds of the variety "Harosoy 63". This application procedure resulted in the equivalent of treating 100 pounds of seeds at dilution rates of 1, 2 and 4 ounces of the active compound. Twenty seeds from each treatment were thereafter planted in pots of soil containing the root rot disease organism *Phytophthora megasperma*. Additional seeds treated with acetone containing no toxicant, were also planted to serve as controls. After planting, the pots containing the seeds were watered and placed in a greenhouse under conditions conducive to the growth of the plants and development of the disease. Two weeks after treatment, the pots were examined to determine the percent kill and control of the disease organism. The results of these examinations are set forth below in Table VI.

TABLE VI

| Test Compound | Dosage in Ounces of Active Compound per 100 Pounds of Seeds | Percent Control Of the Root Rot Organism *Phytophthora megasperma* |
|---|---|---|
| 2,6-Dimethoxy-4-(trichloromethyl)pyridine | 1 | 100 |
| | 2 | 95 |
| | 4 | 80 |
| 2,6-Diethoxy-4-(trichloromethyl)pyridine | 1 | 50 |
| | 2 | 25 |
| | 4 | 25 |
| 2,6-Dibutoxy-4-(trichloromethyl)pyridine | 1 | 25 |
| | 2 | 25 |
| | 4 | 50 |
| 2-Ethoxy-6-methoxy-4-(trichloromethyl)pyridine | 1 | 55 |
| | 2 | 90 |
| | 4 | 85 |
| 2-Butoxy-6-methoxy-4-(trichloromethyl)pyridine | 1 | 55 |
| | 2 | 65 |
| | 4 | 70 |
| Control | — | 25 |

EXAMPLE XV

Acetone dilutions were prepared by admixing predetermined amounts of one of the hereinafter set forth compounds with predetermined amounts of acetone.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying one cubic centimeter (cc) of one of the test dilutions directly onto the soil surface in the pots to give dosages equivalent to 0.125, 0.25, 0.5 and 1.0 pounds per acre in-furrow, based upon treating a 1" band of a crop with a 36" row spacing. After the acetone had evaporated, the soil in the pots was capped with a layer of sterile soil. Additional pots were also prepared as above and sprayed with acetone containing no toxicant to serve as controls. The pots were thereafter maintained under conditions conducive to both plant growth and disease development. Two weeks after treatment, the pots were examined to determine the percent of disease control. The results of this examination are set forth below in Table VII.

The results of this study are set forth below in Table VIII.

TABLE VIII

| Test Compound | Percent Control of Pea Root Rot (*Aphanomyces euteiches*) at Indicated Dosages in Pounds per Acre in-furrow After Indicated Days After Treatment | | | | | | | | | | | |
|---|---|---|---|---|---|---|---|---|---|---|---|---|
| | Days | 12 | | | | 22 | | | | 33 | | | |
| | Dosage | 0.25 | 0.5 | 1.0 | 2.0 | 0.25 | 0.5 | 1.0 | 2.0 | 0.25 | 0.5 | 1.0 | 2.0 |
| 2,6-Dimethoxy-4-(tri-chloromethyl)pyridine | | 75 | 75 | 85 | 55 | 55 | 65 | 65 | 20 | 40 | 50 | 45 | |
| Control | | | 10 | | | | 0 | | | | 0 | | |

TABLE VII

| Test Compound | Dosage in Pounds Per Acre In-furrow of Test Compound | Percent Control Of the Root Rot Organism *Phytophthora megasperma* |
|---|---|---|
| 2,6-Dimethoxy-4-(tri-chloromethyl)pyridine | 0.125 | 90 |
| | 0.25 | 90 |
| | 0.50 | 95 |
| | 1.00 | 95 |
| 2,6-Diethoxy-4-(tri-chloromethyl)pyridine | 0.125 | 60 |
| | 0.25 | 60 |
| | 0.50 | 70 |
| | 1.00 | 50 |
| 2,6-Dibutoxy-4-(tri-chloromethyl)pyridine | 0.125 | 40 |
| | 0.25 | 60 |
| | 0.50 | 65 |
| | 1.00 | 60 |
| 2-Ethoxy-6-methoxy-4-(trichloromethyl)-pyridine | 0.125 | 50 |
| | 0.25 | 85 |
| | 0.50 | 70 |
| | 1.00 | 70 |
| 2-Butoxy-6-methoxy-4-(trichloromethyl)-pyridine | 0.125 | 45 |
| | 0.25 | 90 |
| | 0.50 | 95 |
| | 1.00 | 85 |
| Control | — | 25 |

EXAMPLE XVI

A 10 percent granular mixture is prepared by admixing 2.0 grams of 2,6-dimethoxy-4-(trichloromethyl)pyridine with 0.4 grams of Atlox-846 emulsifier (a proprietary material of Imperial Chemical Industries, U.S., which is a polyoxyethylene sorbitol oleate), 1.6 grams of propylene glycol and 16.0 grams calcined montmorillionite clay.

Soil infected with the pea root rot disease organism *Aphanomyces euteiches* was uniformly mixed and used to fill 3-inch pots. Five Little Marvel pea seeds were planted in each pot, with 4 pots being used per test mixture. The pots were treated by distributing quantities of the above test mixture on the soil surface in each pot to give dosages equivalent to 0.25, 0.5, 1.0 and 2.0 pounds of the active material per acre in-furrow, based upon treating a 1" band of a crop with a 36" row spacing. After treatment, sterile potting soil was added to the pots to cover the granular test mixture. Additional pots were also prepared as above to serve as controls and were treated with the same granular mixture containing no test compound. The pots were thereafter maintained under conditions conducive to good plant growth and disease development. The pots were examined after time periods of 12, 22 and 33 days to determine the percent of disease control at each time period.

EXAMPLE XVII

A study was conducted to determine the amount of phytotoxicity exhibited by 2,6-dimethoxy-4-(trichloromethyl)pyridine toward grass and broadleaf plants.

Aqueous dispersions, containing the equivalent of 1, 2 and 4 ounces of the compound per 10 gallons of the ultimate dispersions, were prepared by admixing the above compound, acetone and Tween 85 in 666 cc of water as follows:

| Ounces per 10 Gallons | Water | Active Compound | Acetone | Tween 85 |
|---|---|---|---|---|
| 1 | 666 | 0.5 grams | 1.5 cc | 15 mg |
| 2 | 666 | 1.0 grams | 3.0 cc | 30 mg |
| 4 | 666 | 2.0 grams | 6.0 cc | 60 mg |

The above dispersions were sprayed onto plots of bentgrass containing small amounts of bluegrass and clover at a rate equivalent of 10 gallons per 100 square feet. At the same time, additional plots were sprayed with an acetone/Tween 85/water mixture containing no toxicant to serve as a control. In addition, a no-treatment control plot was also prepared.

Twenty two hours after treatment, the plots were examined to determine the percent phytotoxicity exhibited by the test compound. The examination indicated that there was the complete absence of any phytotoxic response exhibited by the compound.

EXAMPLE XVIII

Acetone dilutions were prepared by admixing predetermined amounts of 2,6-dimethoxy-4-(trichloromethyl)pyridine with predetermined amounts of acetone. One milliliter aliquots of each dilution were applied equally to 1-ounce seedlots of seeds of each of Little Marvel pea seeds, Early Gallatin beans and Golden Bantam corn. This application procedure resulted in the equivalent of treating 100 pounds of seeds at dilution rates of 0.5, 1 and 2 ounces of the active compound. Twenty seeds from each treatment were thereafter planted in pots of soil containing the root rot disease organism *Phythium ultimum*. Additional seeds, one group treated with acetone alone and a group of untreated seeds, were also planted to serve as controls. After planting, the plots containing the seeds were watered and placed in a greenhouse under conditions conducive to the growth of the plants and development of the disease. Twelve days after treatment, the pots were examined to determine the percent kill and control of the disease organism. The results of these examinations are set forth below in Table IX.

Table IX

| Test Compound | Dosage in Ounces of Active Compound per 100 Pounds of Seeds | Percent Control of Pythium Root Rot After 12 Days in Indicated Crops | | |
|---|---|---|---|---|
| | | Corn | Peas | Beans |
| 2,6-Dimethoxy-4-(trichloromethyl)pyridine | 0.5 | 70 | 55 | 75 |
| | 1.0 | 65 | 55 | 70 |
| | 2.0 | 65 | 80 | 70 |
| Control (Acetone) | — | 34 | 22.5 | 13 |
| No Treatment Control | — | 34 | 19 | 9 |

EXAMPLE XIX

Acetone dilutions were prepared by admixing predetermined amounts of one of the hereinafter set forth compounds with predetermined amounts of acetone.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. Separate pots were treated by spraying one cc of one of the test dilutions directly onto the soil surface in the pot to give dosages equivalent to 0.25, 0.5 and 1.0 pounds per acre in-furrow, based upon treating a 1" band of a crop with a 36" row spacing. After the acetone had evaporated, the soil in the pots was capped with a layer of sterile soil. Additional pots were also prepared as above to serve as controls and sprayed with acetone alone. The pots were thereafter maintained under conditions conducive to both plant growth and disease development. Sixteen days after treatment, the pots were examined to determine the amount of disease control, as evidenced by the number of plants surviving. The results of the examination are set forth below in Table X.

TABLE X

| Compound | Number of Plants of Twenty Surviving at Indicated Dosage | | |
|---|---|---|---|
| | Equivalent Pounds per Acre, In-furrow | | |
| | 1.00 | 0.50 | 0.25 |
| 2,6-Dimethoxy-4-(trichloromethyl)pyridine | 18 | 16 | 13 |
| 2,6-Dimethoxy-4-(dichlorofluoromethyl)pyridine | 18 | 14 | 12 |
| 2,6-Dimethoxy-4-(chlorodifluoromethyl)pyridine | 18 | 11 | 9 |
| 2,6-Dimethoxy-4-(trifluoromethyl)pyridine | 9 | 13 | 10 |
| 2,6-Di-2-propenyl-4-(trichloromethyl)pyridine | 18 | 18 | 18 |
| 2-Ethoxy-6-methoxy-4-(trichloromethyl)pyridine | 18 | 18 | 17 |
| 2-Butoxy-6-methoxy-4-(trichloromethyl)pyridine | 13 | 14 | 12 |
| 2-Methoxy-6-octyloxy-4-(trichloromethyl)pyridine | 13 | 16 | 13 |
| 2-Dodecyloxy-6-methoxy-4-(trichloromethyl)pyridine | 14 | 14 | 9 |
| 2,4-Dimethoxy-6-(trichloromethyl)pyridine | 18 | 18 | 15 |
| 2-Butoxy-4-methoxy-6-(trichloromethyl)pyridine | 15 | 15 | 11 |
| 2,4-Dibutoxy-6-(trichloromethyl)pyridine | 14 | 14 | 9 |
| Control | 3 | 3 | 3 |

EXAMPLE XX

Acetone dilutions were prepared by admixing predetermined amounts of one of the hereinafter set forth compounds with predetermined amounts of acetone.

Soil infected with the pea root rot disease organism *Aphanomyces euteiches* was uniformly mixed and used to fill 3-inch pots. Five Little Marvel pea seeds were planted in each pot with 4 pots being used per test mixture. The pots were treated by spraying one cc of one of the test dilutions directly onto the soil surface in the pots to give dosages equivalent to 0.25, 0.5 and 1.0 pounds per acre in-furrow, based upon treating a 1" band of a crop with a 36" row spacing. After the acetone had evaporated, the soil in the pots was capped with a layer of sterile soil. Additional pots were also prepared as above and sprayed with acetone alone to serve as controls. The pots were thereafter maintained under conditions conducive to both plant growth and disease development. Two weeks after treatment, the pots were examined to determine the amount of disease control, as evidenced by the number of plants surviving. The results of this examination are set forth below in Table XI.

TABLE XI

| Compound | Number of Plants of Twenty Surviving at Indicated Dosage | | |
|---|---|---|---|
| | Equivalent Pounds per Acre, In-furrow | | |
| | 1.00 | 0.50 | 0.25 |
| 2,6-Dimethoxy-4-(trichloromethyl)pyridine | 18 | 15 | 12 |
| 2,6-Dimethoxy-4-(dichlorofluoromethyl)pyridine | 18 | 13 | 12 |
| 2,6-Dimethoxy-4-(chlorodifluoromethyl)pyridine | 17 | 11 | 9 |
| 2,6-Dimethoxy-4-(trifluoromethyl)pyridine | 10 | 14 | 13 |
| 2-Ethoxy-6-methoxy-4-(trichloromethyl)pyridine | 18 | 15 | 13 |
| 2-Butoxy-6-methoxy-4-(trichloromethyl)pyridine | 13 | 13 | 12 |
| 2-Methoxy-6-octyloxy-4-(trichloromethyl)pyridine | 13 | 12 | 11 |
| 2-Methoxy-6-dodecyloxy-4-(trichloromethyl)pyridine | 15 | 13 | 10 |
| 2,4-Dimethoxy-6-(trichloromethyl)pyridine | 14 | 14 | 10 |
| 2-Butoxy-4-methoxy-6-(trichloromethyl)pyridine | 12 | 11 | 10 |
| 2,4-Dibutoxy-6-(trichloromethyl)pyridine | 10 | 10 | 8 |
| 2,6-Di-2-propenyl-4-(trichloromethyl)pyridine | 18 | 18 | 15 |
| 2,6-Dimethoxy-4-(dichloromethyl)pyridine | 13 | 12 | 11 |
| 2,6-Dioctyloxy-4-(trichloromethyl)pyridine | 12 | 11 | 9 |
| Control | 2 | 2 | 2 |

EXAMPLE XXI

Acetone dilutions were prepared by admixing predetermined amounts of one of the hereinafter set forth compounds with predetermined amounts of acetone.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying one cc of one of the test mixtures directly onto the soil surface in the pots to give dosages equivalent to 0.25, 0.5 and 1.0 pounds per acre in-furrow, based upon treating a 1" band of a crop with a 36" row spacing. After the acetone had evaporated, the soil in the pots was capped with a layer of sterile soil. Additional pots were also prepared as above and sprayed with acetone containing no toxicant to serve as controls. The pots were thereafter maintained under conditions conducive to both plant growth and disease development. The pots were examined to determine the amount of disease control, as evidenced by the number of plants surviving, afforded over a long time period, namely 26 days and 36 days after treatment. The results of these examinations are set forth below in Table XII.

EXAMPLE XXII

Acetone dilutions were prepared by admixing predetermined amounts of one of the hereinafter set forth compounds with predetermined amounts of acetone.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying one cc of one of the test mixtures directly onto the soil surface in the pots to give dosages equivalent to 0.25, 0.5 and 1.0 pounds per acre in-furrow, based upon treating a 1" band of a crop with a 36" row spacing. After the acetone had evaporated, the soil in the pots was capped with an additional layer of the infected soil. Additional pots for use as controls were also prepared as above and sprayed with acetone alone. The pots were thereafter maintained under conditions conducive to both plant growth and disease development. The pots were examined to determine the percent disease control, as evidenced by the number of surviving plants, afforded over a long time period, namely 26 days and 36 days after treatment. The results of these examinations are set forth below in Table XIII.

TABLE XII

| | Number of Plants of Twenty Surviving at Indicated Dosage and Time Period | | | | | |
|---|---|---|---|---|---|---|
| | Equivalent Pound per Acre, In-furrow | | | | | |
| | 1.0 | | 0.5 | | 0.25 | |
| Compound | 26 Days | 36 Days | 26 Days | 36 Days | 26 Days | 36 Days |
| 2,6-Dimethoxy-4-(trichloromethyl)pyridine | 19 | 18 | 19 | 17 | 18 | 14 |
| 2,6-Dimethoxy-4-(dichlorofluoromethyl)pyridine | 18 | 11 | 19 | 13 | 18 | 16 |
| 2,6-Dimethoxy-4-(chlorodifluoromethyl)pyridine | 17 | 16 | 17 | 16 | 15 | 14 |
| 2,6-Dimethoxy-4-(trifluoromethyul)pyridine | 19 | 10 | 14 | 13 | 15 | 12 |
| 2-Ethoxy-6-methoxy-4-(trichloromethyl)pyridine | 18 | 13 | 198 | 14 | 19 | 9 |
| 2-Butoxy-6-methoxy-4-(trichloromethyl)pyridine | 20 | 15 | 18 | 13 | 15 | 12 |
| 2-Methoxy-6-octyloxy-4-(trichloromethyl)pyridine | 19 | 16 | 15 | 15 | 17 | 9 |
| 2-Methoxy-6-dodecyloxy-4-(trichloromethyl)pyridine | 18 | 18 | 19 | 19 | 19 | 19 |
| 2,4-Dimethoxy-6-(trichloromethyl)pyridine | 16 | 6 | 17 | 16 | 17 | 17 |
| 2-Butoxy-4-methoxy-6-(trichloromethyl)pyridine | 16 | 7 | 17 | 14 | 15 | 14 |
| 2,4-Dibutoxy-6-(trichloromethyl)pyridine | 18 | 16 | 18 | 18 | 18 | 13 |
| 2,6-Di-2-propenyl-4-(trichloromethyl)pyridine | 19 | 19 | 18 | 17 | 20 | 20 |
| 2,6-Dimethoxy-4-(dichloromethyl)pyridine | 8 | 8 | 19 | 19 | 18 | 16 |
| 2,6-Dioctyloxy-4-(trichloromethyl)pyridine | 12 | 12 | 10 | 9 | 10 | 8 |
| Control | 4 | 2 | 4 | 2 | 4 | 2 |

TABLE XIII

| | Number of Plants of Twenty Surviving at Indicated Dosage and Time Period | | | | | |
|---|---|---|---|---|---|---|
| | Equivalent Pound per Acre, In-furrow | | | | | |
| | 1.0 | | 0.5 | | 0.25 | |
| Compound | 26 Days | 36 Days | 26 Days | 36 Days | 26 Days | 36 Days |
| 2,6-Dimethoxy-4-(trichloromethyl)pyridine | 18 | 16 | 19 | 19 | 18 | 15 |
| 2,6-Dimethyoxy-4-(dichlorofluoromethyl)pyridine | 20 | 16 | 19 | 13 | 18 | 12 |
| 2,6-Dimethoxy-4-(chlorodifluoromethyl)pyridine | 19 | 16 | 19 | 14 | 17 | 14 |
| 2,6-Dimethoxy-4-(trifluoromethyl)pyridine | 18 | 18 | 19 | 16 | 16 | 14 |
| 2-Ethoxy-6-methoxy-4-(trichloromethyl)pyridine | 18 | 18 | 19 | 19 | 20 | 14 |
| 2-Butoxy-6-methoxy-4-(trichloromethyl)pyridine | 19 | 19 | 20 | 17 | 19 | 17 |
| 2-Methoxy-6-octyloxy-4-(trichloromethyl)pyridine | 18 | 14 | 15 | 13 | 16 | 12 |
| 2-Methoxy-6-dodecyloxy-4-(trichloromethyl)pyridine | 19 | 18 | 18 | 18 | 12 | 11 |
| 2,4-Dimethoxy-6-(trichloromethyl)pyridine | 18 | 18 | 18 | 14 | 18 | 17 |
| 2-Butoxy-4-methoxy-6-(trichloromethyl)pyridine | 17 | 14 | 15 | 9 | 18 | 14 |
| 2,4-Dibutoxy-6-(tricloromethyl)pyridine | 17 | 16 | 17 | 11 | 18 | 11 |
| 2,6-Di-2-propenyl-4-(trichloromethyl)pyridine | 18 | 18 | 19 | 17 | 18 | 14 |
| 2,6-Dimethoxy-4-(dichloromethyl)pyridine | 12 | 10 | 17 | 13 | 18 | 17 |
| 2,6-Dioctyloxy-4-(trichloromethyl)pyridine | 19 | 17 | 15 | 11 | 16 | 12 |

TABLE XIII-continued

| | Number of Plants of Twenty Surviving at Indicated Dosage and Time Period | | | | | |
|---|---|---|---|---|---|---|
| | Equivalent Pound per Acre, In-furrow | | | | | |
| | 1.0 | | 0.5 | | 0.25 | |
| Compound | 26 Days | 36 Days | 26 Days | 36 Days | 26 Days | 36 Days |
| Control | 3 | 2 | 3 | 2 | 3 | 2 |

EXAMPLE XXIII

Soil infected with the tobacco black shank pathogen *Phytophthora parasitica* var. nicotianeae was uniformly mixed and placed in the 2-inch pots. To said pots were transplanted four week old tobacco seedlings of the "402" variety which had been grown in pathogen free soil. Test dispersions of each of the compounds 2,6-diallyl-4-(trichloromethyl)pyridine, 2,6-di(2-methyl-2-propenyloxy)-4-(trichloromethyl)pyridine and 2,6-di(2-butenyloxy)-4-(trichloromethyl)pyridine were prepared by dissolving the chemicals in acetone and thereafter diluting the solution with water and a surfactant to prepare dispersions containing 100, 33 and 11 parts by weight of each of the compounds per million parts of the ultimate dispersion (ppm). Thereafter, the various test dispersions were employed to treat separate pots containing the seedlings by pouring 50 cubic centimeters of each of the dispersions onto the soil, assuring root contact with sufficient chemical. Additional pots were treated with an aqueous acetone solution containing no toxicant to serve as controls. After treatments, the plants were maintained under conditions conducive for good plant growth and disease development. Five days, 8 days and 13 days after treatment, the plants were examined for disease control. The results of these examinations are set forth below in Table XIV.

TABLE XIV

| Active Compound Employed | Application Rate in PPM | Percent Control of *Phytophthora parasitica* in Tobacco Seedlings at Indicated Time Period | | |
|---|---|---|---|---|
| | | Day After Treatment | | |
| | | 5 | 8 | 13 |
| 2,6-Di-2-propenyl-4-(trichloromethyl)pyridine | 100 | 100 | 100 | 100 |
| | 33 | 100 | 100 | 75 |
| | 11 | 75 | 50 | 25 |
| 2,6-Di(2-methyl-2-propenyloxy)-4-(trichloromethyl)pyridine | 100 | 50 | 50 | 25 |
| | 33 | 50 | 25 | 25 |
| | 11 | 0 | 0 | 0 |
| 2-6-Di(2-butenyloxy)-4-(trichloromethyl)-pyridine | 100 | 50 | 75 | 50 |
| | 33 | 100 | 50 | 25 |
| | 11 | 0 | 0 | 0 |
| Control | 0 | 0 | 0 | 0 |

EXAMPLE XXIV

Acetone dispersions were prepared by admixing predetermined amounts of one of the hereinafter set forth compounds with predetermined amounts of acetone.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying 5 cubic centimeters of one of the test dilutions directly onto the soil surface in the pots to give dosages equivalent to 0.25, 0.5 and 1.0 pound per acre in-furrow, based upon treating a 1" band of crop with a 36" row spacing. After the acetone had evaporated, the soil in the pots was capped with a layer of sterile soil. Additional pots were also prepared as above and sprayed with acetone alone to serve as controls. The pots were thereafter maintained under conditions conducive to both plant growth and disease development. Twelve days and 35 days after treatment, the pots were examined to determine the degree of disease control, as evidenced by the number of surviving plants. The results of this examination are set forth below in Table XV.

TABLE XV

| | Number of Plants of Twenty Surviving at Indicated Dosage and Time Period | | | | | |
|---|---|---|---|---|---|---|
| | Equivalent Pound per Acre, In-furrow | | | | | |
| | 1.0 | | 0.5 | | 0.25 | |
| Test Compound | 12 Days | 35 Days | 12 Days | 35 Days | 12 Days | 35 Days |
| 2,6-Dimethoxy-4-(trichloromethyl)pyridine | 17 | 14 | 18 | 16 | 17 | 12 |
| 2-Ethoxy-6-methoxy-4-(trichloromethyl)pyridine | 17 | 13 | 17 | 14 | 16 | 14 |
| 2,6-Diethoxy-4-(trichloromethyl)pyridine | 17 | 11 | 18 | 15 | 16 | 9 |
| 2,4-Dimethoxy-6-(trichloromethyl)pyridine | 12 | 9 | 18 | 16 | 17 | 9 |
| 2,6-Dimethoxy-4-(trifluoromethyl)pyridine | 16 | 11 | 17 | 12 | 16 | 12 |
| 2,6-Dimethoxy-4-(dichloromethyl)pyridine | 15 | 4 | 16 | 11 | 16 | 9 |

TABLE XV-continued

| | Number of Plants of Twenty Surviving at Indicated Dosage and Time Period | | | | | |
|---|---|---|---|---|---|---|
| | Equivalent Pound per Acre, In-furrow | | | | | |
| | 1.0 | | 0.5 | | 0.25 | |
| Test Compound | 12 Days | 35 Days | 12 Days | 35 Days | 12 Days | 35 Days |
| 2-Butoxy-6-methoxy-4-(trichloromethyl)pyridine | 17 | 15 | 18 | 16 | 17 | 13 |
| 2-Methoxy-6-octyloxy-4-(trichloromethyl)pyridine | 17 | 16 | 17 | 15 | 17 | 8 |
| 2,6-Dibutoxy-4-(trichloromethyl)pyridine | 18 | 12 | 16 | 7 | 15 | 7 |
| 2,6-Dioctyloxy-4-(tricloromethyl)pyridine | 14 | 8 | 16 | 10 | 16 | 8 |
| 2,6-Di-2-propenyl-4-(trichloromethyl)pyridine | — | — | — | — | 16 | 11 |
| Control | 12 | '5 | 12 | 5 | 12 | 5 |

EXAMPLE XXV

A study was conducted following the practice of the present invention to determine the effectiveness of foliar treatment of the compounds of the present invention in controlling the tobacco black shank pathogen *Phytophthora parasitica* var. *nicotianeae* in tobacco plants.

Test concentrates of each of the compounds 2,6-dimethoxy-4-(trichloromethyl)pyridine and 2-methoxy-6-octyloxy-4-(trichloromethyl)pyridine were prepared by dissolving a predetermined amount of one of the compounds with a predetermined amount of acetone containing a predetermined amount of Tween 85. The final dispersions were prepared by diluting a predetermined amount of the concentrate with a predetermined amount of water. Test dispersions were prepared containing 2400 and 300 ppm of each concentrate.

Four tobacco plants of the variety "402" and 4 of the variety "G-28" were grown in 3-inch pots in sterile soil until they were 8-12 inches tall. The plants were sprayed to run-off with one of the test dispersions with 8 plants being used for each test dispersion. At the same time, an additional 8 plants are treated with an acetone/Tween 85/water solution to serve as controls. Two days after treatment, the plants are inserted into larger containers, with the soil and root balls intact, said containers being filled with soil infected with the tobacco black shank pathogen *Phytophthora parasitica* var. *nicotianeae*. The plants were thereafter maintained under conditions conducive for good plant growth and disease development. Seventeen days after treatment, the plants were examined to determine the percent disease control. The results of this examination are set forth below in Table XVI.

TABLE XVI

| | | Percent Control of *Phytophthora parasitica* in Tobacco Plants | |
|---|---|---|---|
| | | Dosage in PPM | |
| Compound Tested | Tobacco Variety | 300 | 2400 |
| 2,6-Dimethoxy-4-(trichloromethyl)pyridine | 402 | 50 | 67 |
| | G-28 | 67 | 83 |
| 2-Methoxy-6-octyloxy-4-(trichloromethyl)pyridine | 402 | 50 | 67 |
| | G-28 | 50 | 83 |
| Control | 402 | 0 | 0 |
| | G-28 | 33 | 33 |

EXAMPLE XXVI

A study was conducted following the practice of the present invention to determine the effectiveness of applying the active compounds of the present invention as a paint to the stems of tobacco plants to control the tobacco black shank pathogen *Phytophthora parasitica*.

Test gels were prepared by admixing a predetermined amount of 2,6-dimethoxy-4-(trichloromethyl)pyridine in a predetermined amount of Isopar H (a proprietary material of the Exxon Corporation, which material is an isoparaffinic oil having a boiling point from 405°-495° F. and having an unsulfonated residue of 98 volume percent and an aromatic content of 0.3 volume percent) and a predetermined amount of Geopan Geo-10 (a proprietary material of N. L. Industries, which material is an organophilic clay gellant). The final gels contained 0.0, 0.1, 1.0 and 10.0 percent of the active compounds.

Tobacco plants of the G-28 variety about 6 inches tall which had been grown in sterile soil were transplanted, with the soil and root ball intact, into containers containing soil infected with the tobacco black shank pathogen *Phytophthora parasitica* var. *nicotianeae*. The plants were painted around the stem circumference with one of the test gels at a height of about 2 inches above the soil line. Eight plants were used for each treatment dosage. At the same time, additional plants were painted in the same manner with the gel containing no toxicant to serve as a control. After treatment, the plants were maintained under conditions conducive to good plant growth and disease formation. Care was taken not to allow water to contact the stems. Seventeen days after treatment, the plants were examined to determine the present kill and control of the disease organism in the plants. The results of this examination are set forth below in Table XVII.

TABLE XVII

| | Percent Control of *Phytophthora parasitica* at Indicated Dosage Percent of Active Component in Gel | | |
|---|---|---|---|
| Active Compound | 10.0 | 1.0 | 0.1 |
| 2,6-Dimethoxy-4-(trichloromethyl)pyridine | 62.5 | 87.5 | 75 |
| Control | 0 | 0 | 0 |

EXAMPLE XXVII

Acetone dispersions were prepared by admixing predetermined amounts of 2,6-dimethoxy-4-(trichloromethyl)pyridine with predetermined amounts of acetone. Seven by 15-inch trays were filled with sterile sandy loam. Twenty bean seeds of the "Early Gallatin" variety which were infected with the disease organisms *Fusarium solani* and *Phythium ultimum* were planted in two 15-inch rows per tray with 2 trays being used per test mixture. The trays were treated by spraying 2 cc of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Fourteen and 21 days after treatment, the trays were examined to determine the amount of disease control, as evidenced by the number of plants surviving. The results of this examination are set forth below in TABLE XXVIII.

TABLE XXVIII

| | Number of Plants of Forty Surviving at Indicated Dosage and Time Period | | | |
|---|---|---|---|---|
| | Equivalent Pound per Acre, In-furrow | | | |
| | 1.0 | | 0.5 | |
| Test Compound | 14 Days | 21 Days | 14 Days | 21 Days |
| 2,6-Dimethoxy-4-(trichloromethyl)pyridine | 36 | 36 | 39 | 34 |
| Control | | 21 | | 21 |

EXAMPLE XXVIII

Acetone dispersions were prepared by admixing predetermined amounts of 2,6-dimethoxy-4-(trichloromethyl)pyridine with predetermined amounts of acetone. Seven by 15-inch trays were filled with sterile sandy loam. Twenty cotton seeds of the variety "SJ-2" and which were infected with the disease organisms *Phythium ultimum* and *Rhizoctonia solani* were planted in two 15-inch rows in said trays with 2 trays being used per test mixture. The trays were treated by spraying 2 cc of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Eleven and 61 days after treatment, the trays were examined to determine the amount of disease control, as evidenced by the number of plants surviving. The results of this examination are set forth below in TABLE XXIX.

TABLE XXIX

| | Number of Plants of Forty Surviving at Indicated Dosage and Time Period | | | |
|---|---|---|---|---|
| | Equivalent Pound per Acre, In-furrow | | | |
| | 1.0 | | 0.5 | |
| Test Compound | 11 Days | 61 Days | 11 Days | 61 Days |
| 2,6-Dimethoxy-4-(trichloromethyl)pyridine | 31 | 25 | 36 | 25 |
| Control | | 5 | | 5 |

EXAMPLE XXIX

Acetone dispersions were prepared by admixing a predetermined amount of 2,6-dimethoxy-4-(trichloromethyl)pyridine with a predetermined amount of acetone.

Soil infected with the pea root rot organism *Aphanomyces euteiches* was prepared by admixing 2 parts of sterile sandy loam soil with 1 part of soil infected with the above organism. The 1 mixture was uniformly mixed and used to fill 8×30-inch trays. Twenty pea seeds of the variety "Green Giant 81005" were planted in two 30-inch rows in said trays with 2 trays being used per test mixture. The trays were treated by spraying 4 cc of one of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Twelve, 30 and 44 days after treatment, the trays were examined to determine the amount of disease control, as evidenced by the number of plants surviving. The results of this examination are set forth below in TABLE XXX.

TABLE XXX

| Test Compound | Number of Plants of Forty Surviving at Indicated Dosage and Time Period | | | | | |
|---|---|---|---|---|---|---|
| | Equivalent Pound per Acre, In-furrow | | | | | |
| | 1.0 | | | 0.5 | | |
| | 12 Days | 30 Days | 44 Days | 12 Days | 30 Days | 44 Days |
| 2,6-Dimethoxy-4-(trichloromethyl)pyridine | 33 | 15 | 6 | 37 | 17 | 10 |
| Control | 24 | 5 | 3 | 24 | 5 | 3 |

EXAMPLE XXX

Acetone dilutions were prepared by dissolving 2,6-dimethoxy-4-(trichloromethyl)pyridine in predetermined amounts with predetermined amounts of acetone. One milliliter aliquots of each dilution were applied equally to 1-ounce seedlots of pea seeds of the variety "Little Marvel".

This application procedure resulted in an equivalent to treating 100 pounds of seeds at a dilution rate of 1, 2, 4 and 8 ounces of active compound. Forty seeds from each treatment were thereafter planted in 7×15-inch trays of soil containing the root rot disease organism, *Aphanomyces euteiches*. Forty additional seeds treated with acetone containing no toxicant were also planted to serve as controls. After planting, the trays containing the seeds were watered and placed in a greenhouse under conditions conducive to good plant growth and to disease development. Eleven, 22 and 33 days after treatment, the trays were thereafter examined to determine the percent kill and control of the disease organism from each treatment as evidenced by the number of surviving plants. The results of this examination are set forth below in TABLE XXXI.

TABLE XXXI

| Test Compound | Dosage in Ounces of Active Compound per 100 Pounds of Seeds | Number of Plants of Forty Surviving at Indicated Dosage and at Indicated Time Period | | |
|---|---|---|---|---|
| | | 11 Days | 22 Days | 33 Days |
| 2,6-Dimethoxy-4-(trichloromthyl)pyridine | 1.0 | 33 | 16 | 15 |
| | 2.0 | 33 | 15 | 6 |
| | 4.0 | 33 | 18 | 8 |
| | 8.0 | 33 | 16 | 4 |
| Control | — | 17 | 10 | 4 |

What is claimed is:

1. A substantially pure compound corresponding to the formula

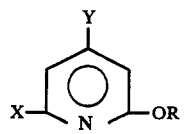

wherein X and Y represent OR', trichloromethyl, trifluoromethyl, dichloromethyl, dichlorofluoromethyl or chlorodifluoromethyl with the proviso that one of X or Y must be OR' and the other of X and Y is other than OR'; and R and R' each independently represent alkyl of 1 to 12 carbon atoms or alkenyl of 3 or 4 carbon atoms.

2. A compound as defined in claim 1 wherein X is OR'.

3. A compound as defined in claim 1 wherein Y is OR'.

4. A compound as defined in claim 2 wherein Y is trichloromethyl.

5. A compound as defined in claim 3 wherein X is trichloromethyl.

6. The compound as defined in claim 4 which is 2,6-dimethoxy-4-(trichloromethyl)pyridine.

7. The compound as defined in claim 4 which is 2,6-diethoxy-4-(trichloromethyl)pyridine.

8. The compound as defined in claim 4 which is 2-ethoxy-6-methoxy-4-(trichloromethyl)pyridine.

9. The compound as defined in claim 4 which is 2-butoxy-6-methoxy-4-(trichloromethyl)pyridine.

10. The compound as defined in claim 4 which is 2,6-di-2-propenyloxy-4-(trichloromethyl)pyridine.

11. The compound as defined in claim 5 which is 2,4-dimethoxy-6-(trichloromethyl)pyridine.

12. A fungicidal composition comprising a fungicidally-effective amount of a compound corresponding to the formula

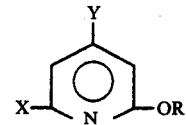

wherein X and Y represent OR', trichloromethyl, trifluoromethyl, dichloromethyl, dichlorofluoromethyl or chlorodifluoromethyl with the proviso that one of X or Y must be OR' and the other of X and Y is other than OR'; and R and R' each independently represent alkyl of 1 to 12 carbon atoms or alkenyl of 3 or 4 carbon atoms, in intimate admixture with an inert adjuvant therefor.

13. A composition as defined in claim 12 wherein X is OR'.

14. A composition as defined in claim 12 wherein Y is OR'.

15. A composition as defined in claim 13 wherein Y is trichloromethyl.

16. A composition as defined in claim 14 wherein X is trichloromethyl.

17. The composition as defined in claim 15 in which the compound is 2,6-dimethoxy-4-(trichloromethyl)pyridine.

18. The composition as defined in claim 15 in which the compound is 2,6-diethoxy-4-(trichloromethyl)pyridine.

19. The composition as defined in claim 15 in which the compound is 2-ethoxy-6-methoxy-4-(trichloromethyl)pyridine.

20. The composition as defined in claim 15 in which the compound is 2-butoxy-6-methoxy-4-(trichloromethyl)pyridine.

21. The composition as defined in claim 15 in which the compound is 2,6-di-2-propenyloxy-4-(trichloromethyl)pyridine.

22. The composition as defined in claim 16 in which the compound is 2,4-dimethoxy-6-(trichloromethyl)pyridine.

23. A method for protecting plants from plant fungal disease organisms which attack the plant root system which comprises contacting plants, plant parts or their habitat with a non-phytotoxic, plant protecting amount of a plant protectant corresponding to the formula

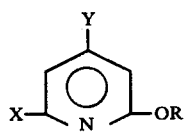

wherein X and Y represent OR', trichloromethyl, trifluoromethyl, dichloromethyl, dichlorofluoromethyl or chlorodifluoromethyl with the proviso that one of X or Y must be OR' and the other of X and Y is other than OR'; and R and R' each independently represent alkyl of 1 to 12 carbon atoms or alkenyl of 3 or 4 carbon atoms, in intimate admixture with an inert adjuvant therefor.

24. The method as defined in claim 23 wherein the plants, plant parts or habitat are contacted with the plant protector prior to the plants being attacked by plant root disease organisms.

25. The method as defined in claim 23 wherein the plants, plant parts or habitat are contacted with the plant protector after the plants have been attacked by plant root disease organisms.

26. The method as defined in claim 23 wherein the plant roots are contacted with the plant protectant.

27. The method as defined in claim 23 wherein the above-ground portions of the plants are contacted with the plant protectant.

28. The method as defined in claim 23 wherein plant seeds are contacted with the plant protectant.

29. A method as defined in claim 23 wherein X is OR'.

30. A method as defined in claim 23 wherein Y is OR'.

31. A method as defined in claim 29 wherein Y is trichloromethyl.

32. A method as defined in claim 30 wherein X is trichloromethyl.

33. The method as defined in claim 31 wherein the plant protectant is 2,6-dimethoxy-4-(trichloromethyl)pyridine.

34. The method as defined in claim 31 wherein the plant protectant is 2,6-diethoxy-4-(trichloromethyl)pyridine.

35. The method as defined in claim 31 wherein the plant protectant is 2-ethoxy-6-methoxy-4-(trichloromethyl)pyridine.

36. The method as defined in claim 31 wherein the plant protectant is 2-butoxy-6-methoxy-4-(trichloromethyl)pyridine.

37. The method as defined in claim 31 wherein the plant protectant is 2,6-di-2-propenyl-4-(trichloromethyl)pyridine.

38. The method as defined in claim 32 wherein the plant protectant is 2,4-dimethoxy-6-(trichloromethyl)pyridine.

* * * * *

UNITED STATES PATENT AND TRADEMARK OFFICE
CERTIFICATE OF CORRECTION

PATENT NO. : 4,190,662

DATED : February 26, 1980

INVENTOR(S) : Myk R. Fenstermacher, & Robert L. Noveroske

It is certified that error appears in the above-identified patent and that said Letters Patent are hereby corrected as shown below:

Col. 1, line (between lines 10 and 15) should show formula as follows:

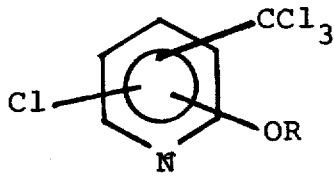

Col. 2, line 57 "one Y'" should read --one of Y'--.

Col. 16, line 29 "incluing" should read --including--.

Col. 17, line 8 "liquid" should read --liquids--.

Col. 19, in table V under heading "Dosage in Pounds" "1.25" should read --0.25--.

Col. 22, in table VIII numerical line reading "75 75 85 55 55 65 65 20 40 50 45" should read ---75 75 85 85 55 55 65 65 20 40 50---.

UNITED STATES PATENT AND TRADEMARK OFFICE
CERTIFICATE OF CORRECTION

PATENT NO. : 4,190,662  Page 2 of 3
DATED : February 26, 1980
INVENTOR(S) : Myk R. Fenstermacher, & Robert L. Noveroske It is certified that error appears in the above-identified patent and that said Letters Patent are hereby corrected as shown below:

Col. 25, in table XII "(trifluoromethyul)" should read --(trifluoromethyl)--

Col. 25, in table XII column "26 days" "198" should read--19--.

Col. 26, in table XIII "2,6-Dimethyoxy" should read --Dimethoxy--.

Col. 26, in table XIII "(tricloromethyl)" should read --(trichloromethyl)--.

Col. 27, line 16 "the" should be deleted.

Col. 27, in table XIV "Day" should read --Days--.

Col. 29, in table XV "(trichloromethyl)" should read --(trichloromethyl)--.

Col. 29, between lines 55 and 60 in Table XVI "parsitica" should read --parasitica--.

UNITED STATES PATENT AND TRADEMARK OFFICE
CERTIFICATE OF CORRECTION

PATENT NO. : 4,190,662

DATED : February 26, 1980

INVENTOR(S) : Myk R. Fenstermacher, & Robert L. Noveroske

It is certified that error appears in the above-identified patent and that said Letters Patent are hereby corrected as shown below:

Col. 33, between lines 40 and 45 (Table XXXI)
"(chloromthyl)" should read -(chloromethyl)-

Signed and Sealed this

Fifteenth Day of July 1980

[SEAL]

Attest:

SIDNEY A. DIAMOND

Attesting Officer

Commissioner of Patents and Trademarks